United States Patent [19]
Thyagarajan

[11] 3,987,034
[45] Oct. 19, 1976

[54] PROCESS FOR THE PREPARATION OF TETRAZOCINE DERIVATIVES

[75] Inventor: Budular Subbanarayanan Thyagarajan, San Antonio, Tex.

[73] Assignee: Idaho Research Foundation, Inc., Moscow, Idaho

[22] Filed: Mar. 11, 1974

[21] Appl. No.: 450,002

[52] U.S. Cl. .................. 260/239 BC; 260/239 HM; 260/239 BE
[51] Int. Cl.² ...................................... C07D 259/00
[58] Field of Search ............... 260/239 BC, 239 BE, 260/239 AM

[56] References Cited
UNITED STATES PATENTS
3,448,103   6/1969   Van Doesburgh et al.... 260/239 BC Primary Examiner—Leland A. Sebastian

[57] ABSTRACT

A process for the conversion of a pentamethylenetetramine derivative into the corresponding tetrazocine derivative by nitrating said pentamethylenetetramine derivative at room temperature. The tetrazocine derivative is an effective intermediate in the manufacture of the explosive, HMX.

12 Claims, No Drawings

PROCESS FOR THE PREPARATION OF TETRAZOCINE DERIVATIVES

BACKGROUND AND SUMMARY OF THE INVENTION

The present invention relates to a process for the conversion of pentamethylenetetramine derivatives into the corresponding tetrazocine derivatives. More particularly, the present invention is directed to a process for selectively cleaving the bicyclononane system to form tetrazocine derivatives, which derivatives preferably have two N-NO₂ functions. Examples of the tetrazocine derivatives prepared in accordance with the present invention include, among others, 1,5-diacetyl-3,7-dinitrooctahydrotetrazocine (prepared by selectively cleaving 1,5-diacetyl-1,3,5,7-tetraazabicyclo[3.3.1]nonane); 1,5-disulfonyl-3,7-dinitrooctahydrotetrazocine (prepared by selectively cleaving 1,5-disulfonyl-1,3,5,7-tetraazabicyclo[3.3.1]nonane); 1,5-dibenzoyl-3,7-dinitrooctahydrotetrazocine (prepared by selectively cleaving 1,5-dibenzoyl-1,3,5,7-tetraazabicyclo[3.3.1]nonane); and 1,5-di(trichloroacetyl)-3,7-dinitrooctahydrotetrazocine (prepared by selectively cleaving 3,7-di(trichloroacetyl)-1,3,5,7-tetraazabicyclo[3.3.1]nonane). The above tetrazocine derivatives are effective intermediates for the preparation of 1,3,5,7-tetranitrooctahydrotetrazocine, hereinafter referred to as HMX, which is a high melting explosive of great commercial value.

All of the presently known and used methods of manufacturing HMX were developed during World War II. These methods employ hexamethylenetetramine as the starting material. Nitrolysis of this compound produces mixtures of the six-membered ring compound cyclotrimethylenetrinitramine, hereinafter referred to as RDX, and HMX, together with minor amounts of other open chain products. Existing methods produce large amounts of RDX (a valuable explosive) with HMX being obtained in only very small yields. There is an ever-increasing interest in producing HMX as the sole product from such nitrolysis reactions so that the expensive procedures required to separate HMX from RDX can be avoided. In addition, the cost of production should be competitive with presently available methods.

In the synthesis of HMX preferentially from hexamethylenetetramine, the key step is the selective cleavage of the bridgbon between the 1- and 5-positions. The most efficient way to obtain the eight-membered HMX compound is to convert hexamine (hexamethylenetetramine) into the tetraazabicyclo(3,3,1)nonane system and then to selectively cleave the bridge methylene to produce the eight-membered ring. This method would have obvious advantages over any attempts to synthesize HMX directly from other simpler building blocks due to the well-known reluctance of open chain compounds to form rings larger than six-membered rings.

Accordingly, an object of the present invention is to provide an improved process by which a pentamethylenetetramine derivative can be converted into the corresponding tetrazocine derivative.

Another object of the present invention is to provide an improved process for the preparation of tetrazocine derivatives which are effective intermediates in the subsequent preparation of the explosive HMX.

A further object of the present invention is to produce HMX by converting a bicyclononane system into an eight-membered structure and then converting said structure into HMX.

Other objects and further scope of applicability of the present invention will become apparent from the detailed description given hereinafter; it should be understood, however, that the detailed description and specific examples, while indicating preferred embodiments of the present invention, are given by way of illustration only, since various changes and modifications within the spirit and scope of the invention will become apparent to those skilled in the art from this detailed description.

Pursuant to the present invention, it has been found that the above-mentioned disadvantages may be eliminated and a much improved method for producing particular tetrazocine derivatives as intermediates for the subsequent preparation of the explosive HMX can be obtained by nitrolyzing a pentamethylenetetramine derivative into the corresponding dinitro-diacyl, dinitro-disulfonyl, dinitro-di(trichloroacetyl), dinitro-dibenzoyl, dinitro-dinitroso, or other such octahydrotetrazocine compound. Thus, the present invention is concerned with an improved method for producing 1,5-diacetyl-3,7-dinitrooctahydrotetrazocine, hereinafter referred to as DADNT, in high yields and substantially free from other compounds by nitrolyzing a tetraazabicyclo(3,3,1)-nonane derivative, that is, 1,5-diacetyl-1,3,5,7-tetraazabicyclo-(3,3,1)nonane, hereinafter referred to as DAPT or diacrtylpentamethylenetetramine. The method is concerned also with producing related octahydrotetrazocine compounds such as 1,5-dinitroso-3,7-dinitrooctahydrotetrazocine by nitrolyzing 1,5-dinitroso-3,7-tetraazabicyclo[3.3.1]nonane, hereinafter referred to as DNPT or dinitrosopentamethylenetetramine. Still other octahydrotetrazocine compounds produced in accordance with the present invention include 1,5-disulfonyl-3,7-dinitrooctahydrotetrazocine; 1,5-di-(trichloroacetyl)-3,7-dinitrooctahydrotetrazocine; 1,5-dibenzoyl-3,7-dinitrooctahydrotetrazocine and the like.

The present process produces a yield as high as about 75% of the above tetrazocine derivatives. Moreover, the tetrazocine derivatives are substantially free from other compounds, such as RDX, and have a high level of purity which makes them readily convertible to HMX without any further purification being required. The present process eliminates the prior art problems of forming large amounts of the six-membered ring products and open chain products by producing in high yield a water insoluble, readily isolatable, eight-membered ring product which already has two N-NO₂ functions. Furthermore, no other side products are formed in the reaction.

The pentamethylenetetramine derivatives, for example, DNPT or DAPT are nitrolyzed by reacting them with dinitrogen tetroxide, fuming nitric acid, nitric acid or an inorganic nitrate, for example the alkali metal nitrates. Suitable alkali metal nitrates include sodium nitrate or potassium nitrate or mixtures thereof. Advantageously, the nitric acid or inorganic nitrates are mixed with concentrated sulfuric acid and then said solution is added to the pentamethylenetetramine derivative. The addition of said reagents effects the selective cleavage of the bicyclononane system to the tetrazocine derivative.

The present process, unlike the other prior art methods, requires neither cooling nor heating of the reaction mixture either during the addition or during the aging steps of the process and thus the present process can be conducted at ambient temperatures. This, of course, results in a considerable financial savings when the tetrazocine derivative of the present invention is produced on a commercial scale.

The resulting product, for example, 1,5-diacetyl-3,7-dinitrooctahydrotetrazocine can be subsequently converted into the explosive HMX by reacting it with concentrated nitric acid, for example, 99% nitric acid at room temperature. The high yield of DAPT from hexamine (about 99%) makes the present process a valuable method in the production of HMX, completely free of RDX and other open chain derivatives. As a matter of fact, the present invention provides for the non-isolation or purification of the intermediate DADNT in its further conversion to HMX.

The following examples are given merely as being illustrative of the present invention and are not to be considered as limiting.

EXAMPLE 1

To a suspension of 4.1g of potassium nitrate in 10 ml. of concentrated sulfuric acid (specific gravity 1.84) maintained at 25° to 27° C. is added 2.12g of 1,5-diacetyl-1,3,5,7-tetraazabicyclo(3,3,1)nonane (DAPT or diacetylpentamethylenetetramine), with stirring over a period of 12 minutes so that the temperature does not rise above 27° C. After completion of the addition, the mixture is stirred for an additional hour and then poured into 250 ml. of ice water. The solution is then treated with potassium carbonate to a pH of 8 whereby a white solid is precipitated. The precipitate is filtered, washed thoroughly with cold water and dried in air and in a vacuum. A yield of 2.0g is recovered with a melting point of 261° C. The NMR peaks are: delta 2.3 (6 protons): delta 5.56 (8 protons). The calculated elemental analysis is 33.10% carbon, 4.82% hydrogen and 28.96% nitrogen. The analysis of the product showed 33.38% carbon, 4.95% hydrogen and 29.11% nitrogen. The resulting product, which is 1,5-diacetyl-3,7-dinitrooctahydrotetrazocine, is recrystallizable from hot nitromethane and melts at 262.5° to 263.5° C. after recrystallization.

EXAMPLE 2

The procedures in this Example are essentially the same as in the preceding example with the exception that the amounts of reactants are changed to 2.12g of DAPT, 20 ml. of concentrated sulfuric acid and 8.2g of potassium nitrate. The resulting product is much more pure in this reaction than in Example 1. A yield of 2.1g of dinitrodiacetyloctahydrotetrazocine (DADNT) is recovered with a melting point of 261.5° C.

EXAMPLES 3, 4, 5 and 6

The operation of these examples is essentially the same as the previous examples with the exception that the reaction time after the addition of the reactants is varied. The results of these examples are summarized in the accompanying Table I.

TABLE I

Variation reaction time in nitrolytic cleavage
REACTANTS: DAPT = 2.12g. Sulfuric acid 20 ml. $KNO_3$ 8.2g.

| Experiment No. | Addition period | Stirring period | Yield of DADNT | m.p. ° C. |
|---|---|---|---|---|
| 3 | 12 minutes | 25 minutes | 1.5g | 258–259° |
| 4 | 12 minutes | 1hr.15 minutes | 2.1g | 261.5° |
| 5 | 12 minutes | 1hr.30 minutes | 1.92g | 261° |
| 6 | 12 minutes | 1hr.45 minutes | 1.90g | 261.5° |

EXAMPLE 7

The operation of this example is essentially the same as Example 2 with exception that instead of using 8.2g of potassium nitrate, a mixture of 4.1g of potassium nitrate and 3.4g of sodium nitrate is employed. The yield of the product DADNT is 2.1g containing a melting point of 261° C.

EXAMPLE 8

This example is identical to Example 7 with the exception that instead of using a mixture of potassium nitrate and sodium nitrate, only 6.4g of sodium nitrate was utilized. The yield of the product DADNT is 2.05g containing a melting point of 261.5 to 262° C.

EXAMPLE 9

To a vigorously stirred solution of 4.2 ml of 70% nitric acid in 12 ml. of concentrated sulfuric acid (specific gravity of 1.84) is added 2.12g (0.01 mole) of DAPT, over a period of 12 minutes and while maintaining the temperature between 25° and 30° C. After stirring for an additional hour at about 25° to 30° C., the reaction mixture is poured into 250 ml. of ice water. The solution is then made alkaline by adding potassium carbonate and the precipitated solid is filtered, washed thoroughly with water and dried. A yield of 2.32g (80%) of DADNT is recovered with a melting point of between 264° and 265° C. It should be noted that the conversion of DAPT to DADNT using nitric acid rather than alkali metal nitrates produces a greater yield of DADNT.

EXAMPLES 10 to 14

Nitrolysis of DAPT is carried out under different conditions by varying the strength of the nitric acid, the volume of the acid used and the reaction period. The results are shown in Table II.

TABLE II

Nitrolysis of DAPT with a solution of $HNO_3$ in $H_2SO_4$ at 25–30° to produce DADNT
(2.12 g of DAPT is used in each Example)

| Example No. | % of $HNO_3$ used | Volume of $HNO_3$ used (ml) | Volume of $H_2SO_4$* used (ml) | Time for addition (minutes) | Time for Stirring (minutes) | Yield of DADNT | % Yield of DADNT | MP of DADNT |
|---|---|---|---|---|---|---|---|---|
| 9 | 70 | 4.2 | 12 | 12 | 60 | 2.32 | 80 | 264–5° (d) |
| 10 | 70 | 6 | 10 | 12 | 60 | 2.13 | 73.4 | 265° (d) |
| 11 | 90 | 4.2 | 12 | 12 | 60 | 2.18 | 75.2 | 264–5° (d) |
| 12 | 99 | 4.2 | 12 | 12 | 43 | 2.21 | 76.2 | 265° (d) |
| 13 | 99 | 4.2 | 12 | 12 | 60 | 2.25 | 77.6 | 264–5° (d) |

TABLE II-continued

Nitrolysis of DAPT with a solution of $HNO_3$ in $H_2SO_4$ at 25–30° to produce DADNT
(2.12 g of DAPT is used in each Example)

| Example No. | % of $HNO_3$ used | Volume of $HNO_3$ used (ml) | Volume of $H_2SO_4$* used (ml) | Time for addition (minutes) | Time for Stirring (minutes) | Yield of DADNT | % Yield of DADNT | MP of DADNT |
|---|---|---|---|---|---|---|---|---|
| 14 | 99 | 4.2 | 12 | 12 | 75 | 2.12 | 73.1 | 265° (d) |

*Specific gravity of $H_2SO_4$ = 1.84

Examples 1 to 14 indicate that an optimum time is established for producing a maximum yield of the tetrazocine derivative from the bicyclononane derivative.

EXAMPLES 15–16

The procedures in these examples are essentially the same as in Example 1 with the exception that DNPT and disulfonylpentamethylenetetramine, respectively, is used in place of the di-(trichloroacetyl)pentamethytetramine. The resulting products are substantially pure 1,5-dinitroso-3,7-dinitrooctahydrotetrazocine and 1,5-disulfonyl-3,7-dinitrooctohydrotetrazocine, respectively.

EXAMPLE 17

A suspension of 0.80g of 1,5-di(trichloroacetyl)-1,3,5,7-tetraazabicyclo[3.3.1.]nonane in 5ml. of liquid dinitrogen tetroxide was stirred in a closed container for 20 hours. The reaction mixture was poured into ice water and the solution was neutralized with potassium carbonate to give a solid precipitate which when recrystallized from nitromethane melted at 234°–235°; yield, 0.41 g. (43%) of 1,5-di(trichloroacetyl)-3,7-dinitrosooctahydrotetrazocine. Upon further treatment of the above precipitate with 4 ml. of 99% nitric acid at room temperature with stirring for 12 minutes, followed by quenching in 250 ml. ice and neutralization with potassium carbonate to a pH of about 8, a yield of 89% of 1,5-di(trichloroacetyl)-3,7-dinitrooctahydrotetrazocine was obtained. The melting point of the product when recrystalized from hot nitromethane was 275°–278° C. and the NMR peak was delta 6.05 (in acetone —$d_6$). The calculated elemental analysis is 19.34% carbon, 1.62% hydrogen and 16.91% nitrogen. The analysis of the product showed 19.22% carbon, 1.56% hydrogen and 16.82% nitrogen.

EXAMPLE 18

The procedures in this Example are essentially the same as in the preceding example with the exception that 1,5-dibenzoyl-1,3,5,7-tetraazabicyclo[3.3.1]nonane was used in place of 1,5-di-(trichloroacetyl)-1,3,5,7-tetraazabicyclo[3.3.1]nonane and that sodium acetate was added to the reaction mixture to reduce the acidity of the liquid dinitrogen tetroxide. The resulting product is 1,5-dibenzoyl-3,7-dinitro-tetrazocine.

The invention being thus described, it will be obvious that the same may be varied in many ways. Such variations are not to be regarded as a departure from the spirit and scope of the invention, and all such modifications are intended to be included within the scope of the following claims.

It is claimed:

1. A process for selectively cleaving a pentamethylenetetramine derivative into dinitrooctahydrotetrazocine corresponding dinitroctahydrotetrazocine compound which comprises nitrating said derivative at room temperature with dinitrogen tetroxide, fuming nitric acid, nitric acid or an inorganic nitrate.

2. The process of claim 1, wherein the nitrating agent is mixed with sulfuric acid.

3. The process of claim 1, wherein the pentamethylenetetramine derivative is 1,5-diacetyl-1,3,5,7-tetraazabicyclo(3.3.1)-nonane and the corresponding tetrazocine compound is 1,5-diacetyl-3,7-dinitrooctahydrotetrazocine.

4. The process of claim 1, wherein the pentamethylenetetramine derivative is 1,5-disulfonyl-1,3,5,7-tetraazabicyclo(3.3.1)-nonane and the corresponding tetrazocine compound is 1,5-disulfonyl-3,7-dinitrooctahydrotetrazocine.

5. The process of claim 1, wherein the pentamethylenetetramine derivative is 1,5-di(trichloroacetyl)-1,3,5,7-tetraazabicyclo-(3.3.1)-nonane and the corresponding tetrazocine compound is 1,5-di(trichloroacetyl)-3,7-dinitrooctahydrotetrazocine.

6. The process of claim 1, wherein the pentamethylenetetramine derivative is 1,5-dinitroso-1,3,5,7-tetraazabicyclo(3.3.1)-nonane and the corresponding tetrazocine compound is 1,5-dinitroso-3,7-dinitrooctahydrotetrazocine.

7. The process of claim 1, wherein the pentamethylenetetramine derivative is 1,5-dibenzoyl-1,3,5,7-tetraazabicyclo(3.3.1)-nonane and the corresponding tetrazocine compound is 1,5-dibenzoyl-3,7-dinitrooctahydrotetrazocine.

8. The process of claim 1, wherein the inorganic nitrate is selected from the group consisting of sodium nitrate, potassium nitrate and mixtures thereof.

9. The process of claim 1, wherein dinitrooctahydrotetrazocine is converted into HMX by further treatment with nitric acid at room temperature.

10. The process of claim 1, wherein said tetrazocine compound is precipitated from the acid solution by adding an alkaline material thereto.

11. The process of claim 1, wherein after the addition of the nitrating agent the solution is further aged with stirring.

12. A process for selectively cleaving the methylene bridge of 1,5-diacetyl-1,3,5,7-tetraazabicyclo(3.3.1-)nonane into 1,5-acetyl-3,7-dinitrooctahydrotetrazocine which comprises treating said nonane derivative with a mixture of 70% nitric acid and concentrated sulfuric acid at room temperature.

* * * * *